(12) United States Patent
Berke

(10) Patent No.: US 11,134,839 B2
(45) Date of Patent: Oct. 5, 2021

(54) SYSTEM INVERTING CONTROLLER FOR LASER SCANNING SYSTEMS

(71) Applicant: Alcon Inc., Fribourg (CH)

(72) Inventor: Jeremy Krisel Berke, Rockville Center, NY (US)

(73) Assignee: Alcon Inc., Fribourg (CH)

( * ) Notice: Subject to any disclaimer, the term of this patent is extended or adjusted under 35 U.S.C. 154(b) by 144 days.

(21) Appl. No.: 16/266,136

(22) Filed: Feb. 4, 2019

(65) Prior Publication Data

US 2019/0246897 A1 Aug. 15, 2019

Related U.S. Application Data

(60) Provisional application No. 62/628,620, filed on Feb. 9, 2018.

(51) Int. Cl.
| | | |
|---|---|---|
| *A61B 3/00* | (2006.01) | |
| *A61B 3/10* | (2006.01) | |
| *A61F 9/008* | (2006.01) | |
| *G02B 26/10* | (2006.01) | |

(52) U.S. Cl.
CPC ............ *A61B 3/102* (2013.01); *A61B 3/0008* (2013.01); *A61B 3/0025* (2013.01); *G02B 26/101* (2013.01); *G02B 26/105* (2013.01); *A61F 2009/00844* (2013.01); *A61F 2009/00851* (2013.01)

(58) Field of Classification Search
CPC ..... A61B 3/102; A61B 3/0008; A61B 3/0025; A61B 3/0075; A61B 3/10; A61B 3/1025; A61F 2009/00851; A61F 9/008; A61F 2009/00844; G02B 26/10; G02B 26/101; G02B 26/105
See application file for complete search history.

(56) References Cited

U.S. PATENT DOCUMENTS

| | | | | |
|---|---|---|---|---|
| 3,904,961 | A * | 9/1975 | Vieri | G01R 15/005 324/125 |
| 8,262,646 | B2 * | 9/2012 | Frey | A61F 9/00827 606/4 |
| 2005/0159662 | A1 * | 7/2005 | Imanishi | A61B 3/1025 600/473 |
| 2005/0254008 | A1 * | 11/2005 | Ferguson | A61B 3/1025 351/205 |
| 2005/0285558 | A1 * | 12/2005 | Watt | G05B 13/041 318/632 |

(Continued)

FOREIGN PATENT DOCUMENTS

| | | |
|---|---|---|
| WO | WO2005114348 A2 | 12/2005 |
| WO | WO2015100422 A1 | 7/2015 |

*Primary Examiner* — Jordan M Schwartz

(57) ABSTRACT

In certain embodiments, an ophthalmic diagnostic system includes a laser source, a galvanometer, and a system inverting controller (SIC) coupled to the galvanometer. The galvanometer includes one or more optical elements and one or more galvanometer controllers configured to manipulate an orientation of the one or more optical elements to scan the output of the laser source across an ophthalmic target based on galvanometer control signals. The system inverting controller (SIC) is configured to modify input galvanometer control signals based on an estimated transfer function of the galvanometer and provide the modified galvanometer control signals to the galvanometer.

8 Claims, 8 Drawing Sheets

(56) References Cited

U.S. PATENT DOCUMENTS

| | | |
|---|---|---|
| 2011/0069279 A1 | 3/2011 | Hacker |
| 2011/0069366 A1* | 3/2011 | Antkowiak ........ G02B 26/0833 |
| | | 359/200.7 |
| 2012/0184846 A1 | 7/2012 | Izatt |
| 2018/0092527 A1* | 4/2018 | Kuiper ................... A61B 3/102 |
| 2019/0105200 A1* | 4/2019 | Hipsley ................ A61F 9/0017 |
| 2019/0150729 A1* | 5/2019 | Huang ................... A61B 3/102 |

* cited by examiner

SYSTEM INVERTING CONTROLLER FOR LASER SCANNING SYSTEMS

FIELD

The present disclosure relates to laser scanning systems, and more particularly to a system inverting controller for laser scanning systems of ophthalmic diagnostic devices.

BACKGROUND

Optical Coherence Tomography (OCT) is an imaging technique widely adopted in the biomedical fields, including ophthalmology. OCT systems perform high-resolution, cross sectional imaging in semitransparent samples (such as biological tissues) by measuring the echo time delay of reflected light. OCT may be used in ophthalmic diagnostic systems to assist ophthalmic surgeons with precision cutting and/or removal of tissues of an eye such as the vitreous humor. OCT systems use laser scanning systems to scan OCT imaging beams across an eye.

SUMMARY

In certain embodiments, an ophthalmic diagnostic system includes a laser source, a galvanometer, and a system inverting controller (SIC) coupled to the galvanometer. The galvanometer includes one or more optical elements and one or more galvanometer controllers configured to manipulate an orientation of the one or more optical elements to scan the output of the laser source across an ophthalmic target based on galvanometer control signals. The system inverting controller (SIC) is configured to modify input galvanometer control signals based on an estimated transfer function of the galvanometer and provide the modified galvanometer control signals to the galvanometer.

In certain embodiments, a method of scanning a laser of an ophthalmic diagnostic system includes receiving galvanometer control signals at a system inverting controller (SIC) and modifying, by the SIC, the galvanometer control signals based on an estimated transfer function of a galvanometer controller. The method also includes providing the modified galvanometer control signals to a galvanometer, and manipulating, by the galvanometer, one or more optical elements to scan a laser based on the modified galvanometer control signals.

In certain embodiments, a method of configuring a system inverting controller of an ophthalmic diagnostic system includes providing, by a system inverting controller (SIC), command signals to a galvanometer controller based on an initial set of parameters for the SIC, the parameters for the SIC associated with an estimated transfer function of the galvanometer controller. The method also includes receiving, at the SIC, feedback signals from the galvanometer controller, computing a gradient of decent for the initial set of parameters, and modifying the set of parameters based on the gradient of decent. The method further includes determining an amount of variation for the modified set of parameters relative to the initial set of parameters, and in response to a determination that the amount of variation is less than a threshold, storing the modified set of parameters at the SIC.

Certain embodiments may provide one or more technical advantages, in some instances. For example, accuracy of lateral laser scanning, such as in ophthalmic diagnostic devices, may be increased. Ophthalmic procedures, such as OCT imaging or surgical procedures relating to cataracts, may accordingly be improved.

These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
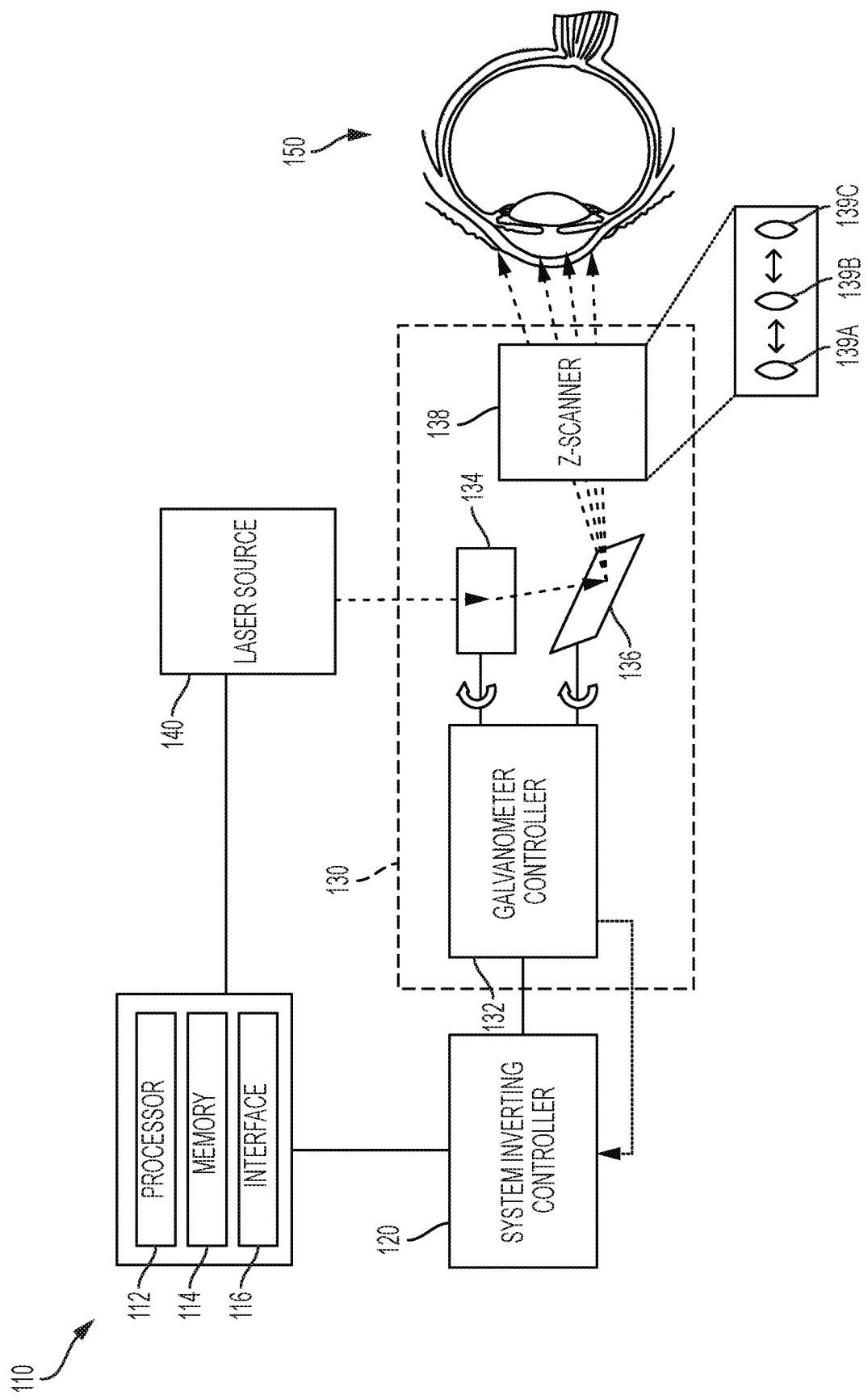
FIG. 1 is a diagram of an example ophthalmic diagnostic system.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

FIG. 1 is a diagram of an example ophthalmic diagnostic system 100. The example system 100 includes a control system 110, a system inverting controller (SIC) 120, a galvanometer 130, and a laser source 140. In the example shown, the ophthalmic diagnostic system 100 is configured to scan a laser output from the laser source 140 across the ophthalmic target 150. The ophthalmic diagnostic system may be an optical coherence tomography (OCT) imaging system, a laser-based surgical system (e.g., LenSx® Laser, WaveLight® F S200 or EX500, all of which are manufactured by Alcon®), or another type of device for determining measurements of the ophthalmic target 150, performing surgical procedures on the ophthalmic target 150, or both.

The example control system 110 generates control signals that are sent to the laser source 140 (e.g., to control a repetition rate or other characteristic of the laser source 140) or the galvanometer 130 via the SIC 120 (e.g., to control a scanning of the laser from the laser source across the ophthalmic target 150). The example control system 110 includes a processor 112, memory 114, and an interface 116. The example processor 112 executes instructions, for example, to generate output data based on data inputs. The instructions can include programs, codes, scripts, or other types of data stored in memory. Additionally, or alternatively, the instructions can be encoded as pre-programmed or re-programmable logic circuits, logic gates, or other types of hardware or firmware components. The processor 112 may be or include a general-purpose microprocessor, as a specialized co-processor or another type of data processing apparatus. In some cases, the processor 112 may be configured to execute or interpret software, scripts, programs, functions, executables, or other instructions stored in the memory 114 to generate control signals for the ophthalmic diagnostic system 100. In some instances, the processor 112 includes multiple processors.

The example memory 114 includes one or more computer-readable media. For example, the memory 114 may include a volatile memory device, a non-volatile memory device, or a combination thereof. The memory 114 can include one or more read-only memory devices, random-access memory devices, buffer memory devices, or a combination of these and other types of memory devices. The memory 114 may store instructions that are executable by the processor 112.

The example interface 116 provides communication between the control system 110 and one or more other devices. For example, the interface 116 may include one or more hardware interfaces that allow interaction with the control system 110 by a user, such as through a keyboard, mouse, touchscreen, and the like. As another example, the interface 116 may include a network interface (e.g., a wireless interface or a wired interface) that allows communication between the control system 110 and the laser source 140, galvanometer 130 (via the SIC 120), or both. The interface 116 may include another type of interface.

The example SIC 120 receives galvanometer control signals from the control system 110, modifies the galvanometer control signals (e.g., signals that control the scanning of the laser across the ophthalmic target 150, such as in a pattern, by the galvanometer 130) based on an estimated transfer function of the galvanometer 130 (as described further below), and provides the modified galvanometer control signal to the galvanometer 130 for execution. The SIC 120 may be implemented as a field-programmable gate array (FPGA) or other type of programmable logic device.

The example galvanometer 130 includes a galvanometer controller 132 that manipulates a set of optical elements (the mirrors 134, 136 and the lenses 139 of the Z-scanner 138) to scan the laser from the laser source 140 based on galvanometer control signals from the control system 110 (via the SIC 120). The galvanometer controller 132 may be implemented as an FPGA device or other type of programmable logic device that converts the galvanometer control signals to a voltage for a motor that manipulates the optical elements to scan the laser. For instance, the galvanometer controller 132 may, based on a galvanometer control signal, manipulate an orientation of the mirror 134 or the mirror 136 to scan the laser in a first and second (e.g., horizontal (x) or vertical (y)) direction, respectively. The galvanometer controller 132 may also, based on a galvanometer control signal, manipulate the position of the lenses 139 with respect to one another to scan the laser in a third direction that is orthogonal to the first and second directions (e.g., the z-direction where the mirrors 134, 136 scan in the x- and y-directions).

The example laser source 140 generates a laser beam for scanning across the ophthalmic target 150. In some embodiments, the laser source 140 is an OCT engine. For example, the ophthalmic diagnostic system 100 may be an OCT system that images aspects of the ophthalmic target 150 (e.g., the cornea, anterior chamber, lens, or other semitransparent body of the ophthalmic target 150) by measuring an echo time delay of light transmitted by the laser source 140 and reflected by the ophthalmic target 150. In some embodiments, the laser source 140 includes a femtosecond laser. For example, where the ophthalmic diagnostic system 100 is a laser-based surgical system, a femtosecond laser of the laser source 140 may generate laser pulses for creating incisions in the ophthalmic target 150 (e.g., the cornea or lens during cataract surgery).

Figure 2A:
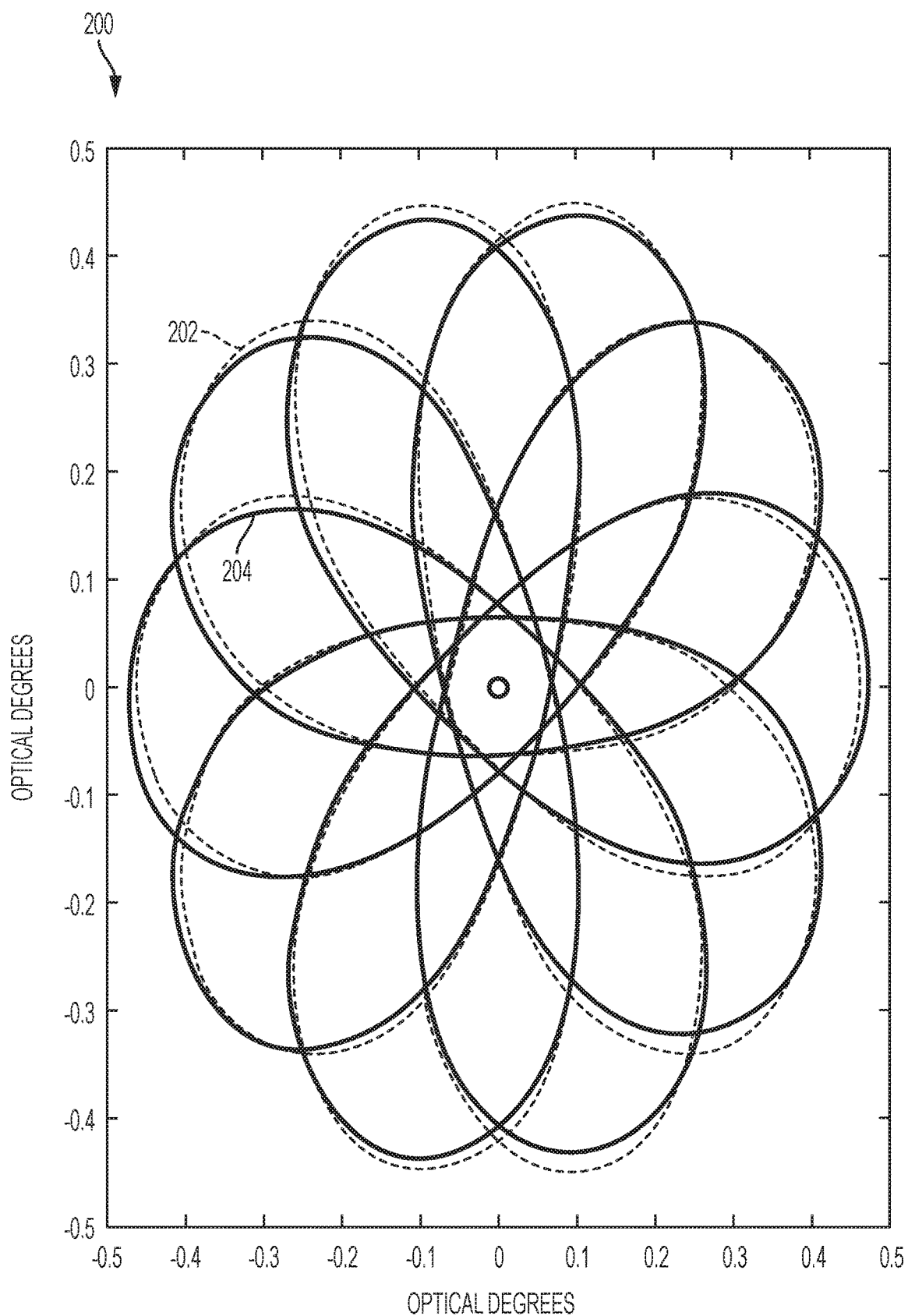
FIG. 2A is a diagram showing an ideal laser scanning pattern and an actual laser scanning pattern for an ophthalmic diagnostic device.
Figure 2B:
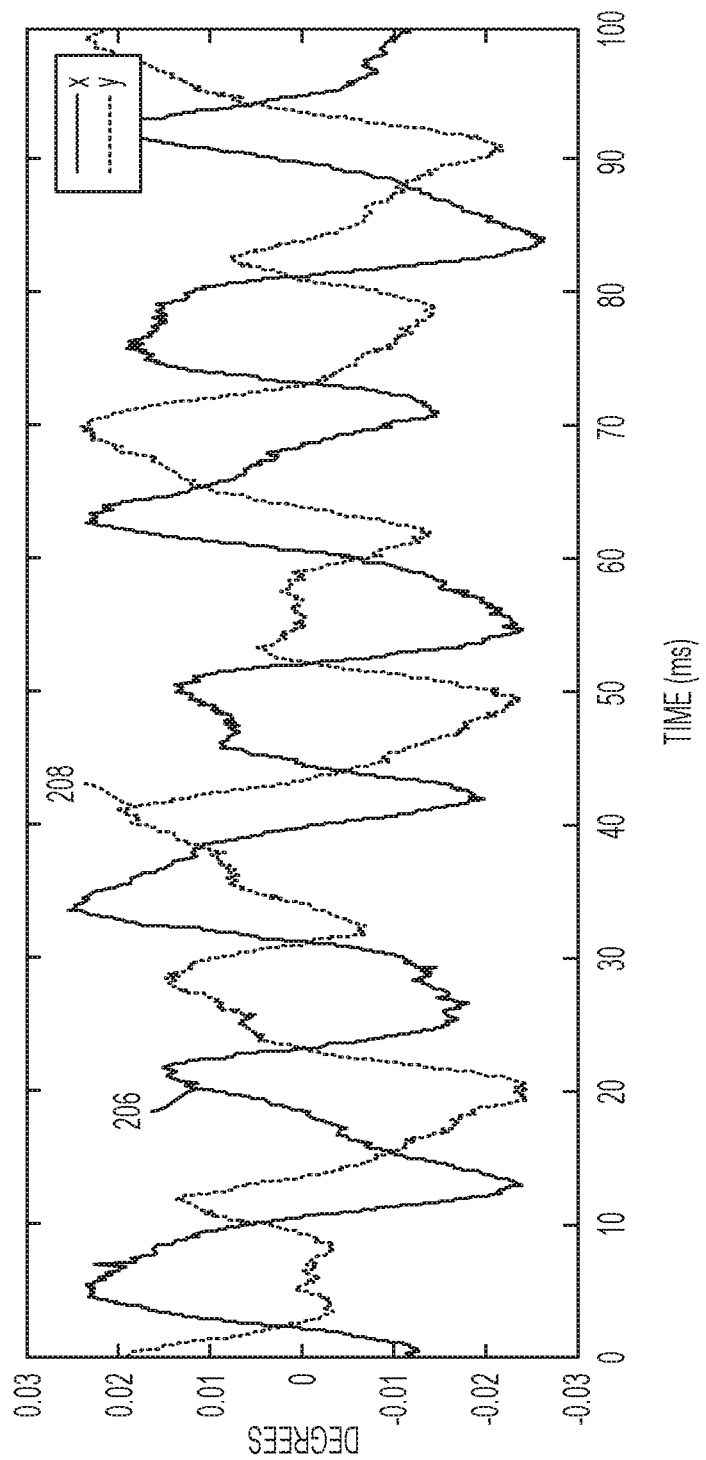
FIG. 2B is a diagram showing example error values for the example actual laser scanning pattern of FIG. 2A relative to the ideal scanning pattern.

FIG. 2A is a diagram showing an ideal laser scanning pattern 202 and an actual laser scanning pattern 204 for an ophthalmic diagnostic device. In the example shown, the ideal laser scanning pattern 202 represents the intended path of a laser beam based on a set of input signals, while the actual laser scanning pattern 204 represents the actual path taken by the laser based on the set of input signals. FIG. 2B is a diagram showing example error values for the example actual laser scanning pattern 204 of FIG. 2A relative to the ideal scanning pattern 202. In particular, the diagram of FIG. 2B shows the error values 206 in an x-direction of the scanning pattern (e.g., the horizontal direction in FIG. 2A), and the error values 208 in a y-direction of the scanning pattern (e.g., the vertical direction in FIG. 2A). In the example shown in FIG. 2B, the error values range between +/−0.03 optical degrees.

As shown in FIGS. 2A-2B, the actual laser scanning pattern 204 varies from the ideal laser scanning pattern 202. In the examples shown, most of the error occurs toward the edges of the scanning pattern (e.g., when the beam is changing directions). At least some of this discrepancy is caused by the galvanometer of the ophthalmic diagnostic system having a certain transfer function that acts on the set of input signals. In some cases, such as the one shown in FIGS. 2A-2B, the low-pass nature of the galvanometer causes this. For instance, at the tips of the petals in the scanning patterns 202, 204, where the direction is changing rapidly, the control signals have high frequency content. Because the galvanometer behaves like a low-pass filter when transforming the input control signals to a beam position, some of the high frequency content of the input control signal is lost. Consequently, the beam position at the tips of the petals in the actual scanning pattern 204 may lose information and no longer resembles the ideal scanning pattern 202.

Figure 3A:
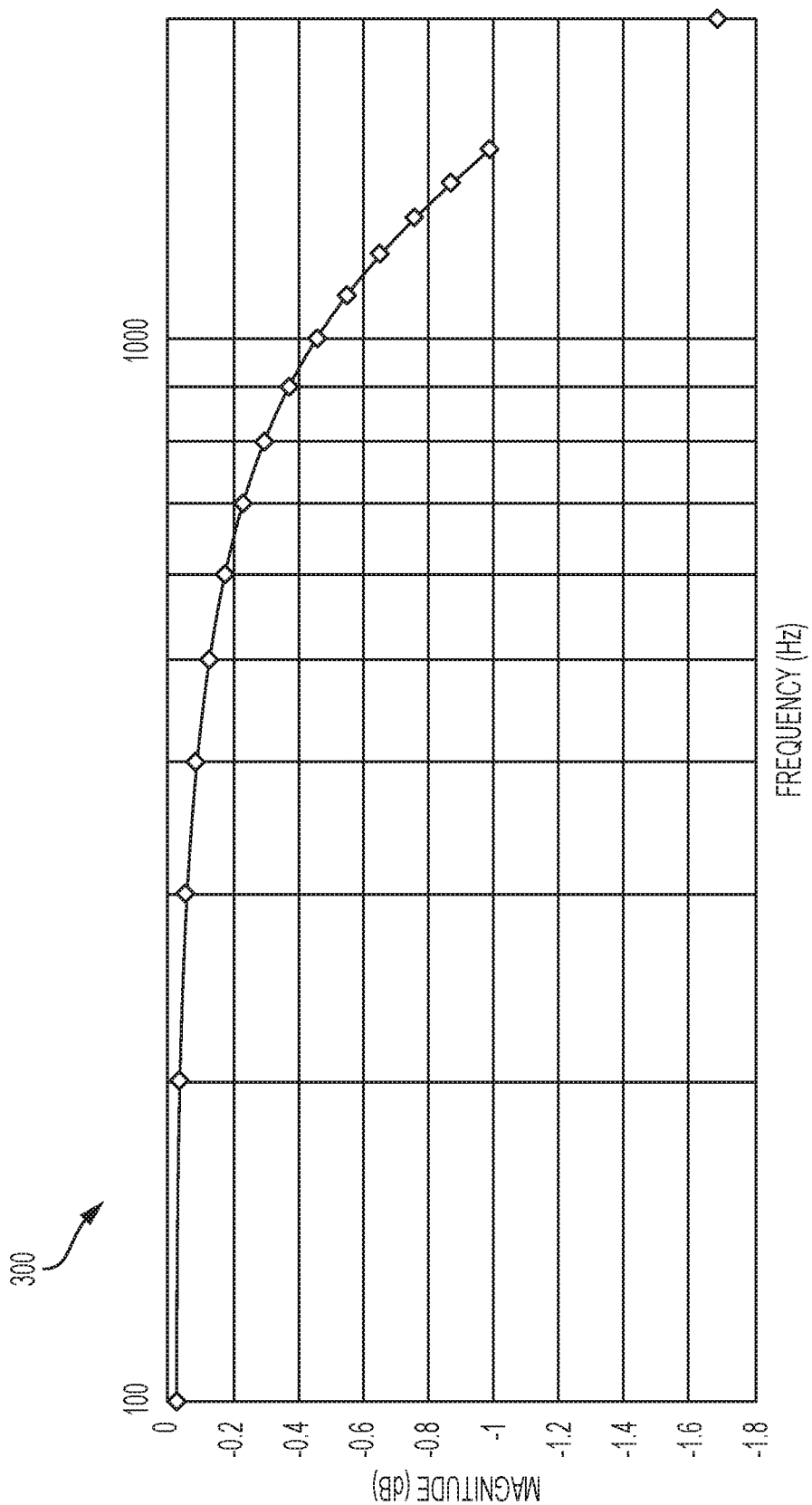
FIG. 3A is a diagram of an example transfer function for a galvanometer.

FIG. 3A is a diagram of an example transfer function 300 for a galvanometer. The transfer function 300 may represent the response of the galvanometer (e.g., the galvanometer 130 of FIG. 1) as a function of frequency for input galvanometer control signals. In the example shown, the transfer function 300 is a low-pass transfer function. However, the transfer function for the galvanometer may be different than the one shown in FIG. 3A. In some cases, the transfer function of a galvanometer may be determined before its implementation/inclusion in an ophthalmic diagnostic and a SIC may be programmed for use in the ophthalmic diagnostic device accordingly. In some cases, the transfer function of the galvanometer is determined at the SIC based on feedback signals from the galvanometer (e.g., the output signals of the galvanometer, which may be compared with the input galvanometer control signals sent to the galvanometer by the SIC).

In some embodiments, the transfer function of a galvanometer can be modeled using a numerical approximation, which may start by noting that the output of a system can be calculated by knowing the transfer function and the input in the s-domain, as follows:

$$y(t) = L^{-1}[(s)X(s)] \quad \text{Eq. (1.1)}$$

where y(t) represents an output voltage, X(s) represents the Laplace domain of an input voltage x(t), and H(s) represents the transfer function of the galvanometer. Because the galvanometer may be modeled as a first order low-pass system, we can use a prototypical transfer function, such as:

$$H(s; k, a) = \frac{ka}{s+a} \quad \text{Eq. (1.2)}$$

where a represents a pole location, and k represents a total gain of the galvanometer system. The transfer function may then be rewritten as a power series:

$$H(s) = k \sum_{n=0}^{\infty} \left(\frac{-s}{a}\right)^n = \left[1 - \frac{s}{a} + \frac{s^2}{a^2} - \ldots\right]; |s| < |a|. \quad \text{Eq. (1.3)}$$

An output may be determined by multiplying by the input and taking the inverse Laplace transform:

$$y(t) = \quad \text{Eq. (1.4a)}$$

$$L^{-1}\left\{k \sum_{n=0}^{\infty} \left(\frac{-s}{a}\right)^n X(s)\right\} = kL^{-1}\left[X(s) - \frac{sX(s)}{a} + \frac{s^2 X(s)}{a^2} - \ldots\right]$$

$$y(t) = k \sum_{n=0}^{\infty} \frac{(-1)^n}{a^n} x^{(n)}(t) \quad \text{Eq. (1.4b)}$$

$$y(t) \approx kx(t) - \frac{k}{a}\frac{dx}{dt} \quad \text{Eq. (1.4c)}$$

From Equation 1.4c, the effect of the first order system can be seen, which may be understood as subtracting some portion of the derivative from the input. Referring to the example scanning pattern shown in FIG. 2A, the input is changing rapidly at the tips of the petals, so the derivative term removes a larger portion of the output than when the beam is moving in a constant direction.

In some embodiments, the transfer function may be modeled by starting with the same prototypical first order transfer function:

$$H(s; k, a) = \frac{ka}{s+a}. \quad \text{Eq. (1.5)}$$

A differential equation which has Equation 1.5 as its transfer function, may be represented by:

$$H(s) = \frac{Y(s)}{X(s)} = \frac{ka}{s+a} \rightarrow Y(s)[s+a] = kaX(s). \quad \text{Eq. (1.6)}$$

By taking the inverse Laplace transform of this equation, a desired equation can be determined. For example:

$$\frac{dy}{dt} + ay = kax \quad \text{Eq. (1.7a)}$$

$$\frac{dy}{dt} = a[kx(t) - y(t)] \quad \text{Eq. (1.7b)}$$

which can be numerically integrated for the function y(t):

$$y_{i+1} = a\Delta t(kx_i - y_i) + y_i. \quad \text{Eq. (1.8)}$$

where a and k are the parameters described above for the first order transfer function of the galvanometer, $x_i$ is the input (and thus, desired output) of the galvanometer, $y_i$ is the output of the SIC, and $\Delta t$ is the elapsed time between t=i and t=i+1. Since there are no derivatives involved in Equation 1.8, any input signal can be used. In some cases, Equation 1.8 may be used as the estimated transfer function for a system inverting controller for a galvanometer.

To compensate for the transfer function of the galvanometer, a SIC with an inverse transfer function may be inserted in the signal chain, such as, for example, before the galvanometer. The output of the system may accordingly be modeled by:

$$y(t) = L^{-1}\{H(s)H^{-1}(s)X(s)\} \quad \text{Eq. (2.1)}$$

Using the above first order approximation of the galvanometer, the inverse transfer function may be $$H^{-1}(s) = \frac{s+a}{ka}. \quad \text{Eq. (2.2)}$$

In effect, the SIC tries to compensate for undesirable effects of the galvanometer being controlled. For example, the SIC may add the derivative of the signal back into the signal in the same proportion that the galvanometer removes it, effectively leaving only the original input signal at the output (the desired condition). The Laplace domain representation of an output signal then becomes:

$$Y(s) = H^{-1}(s) * X(s) = \frac{s+a}{ka} * X(s) \quad \text{Eq. (2.2a)}$$

$$Y(s) = \frac{1}{k}\left[\frac{s * X(s)}{a} + X(s)\right] \quad \text{Eq. (2.2b)}$$

with the corresponding time domain representation being:

$$y(t) = \frac{1}{k}\left[\frac{1}{a}\frac{dx}{dt} + x(t)\right]. \quad \text{Eq. (2.2c)}$$

Figure 3B:
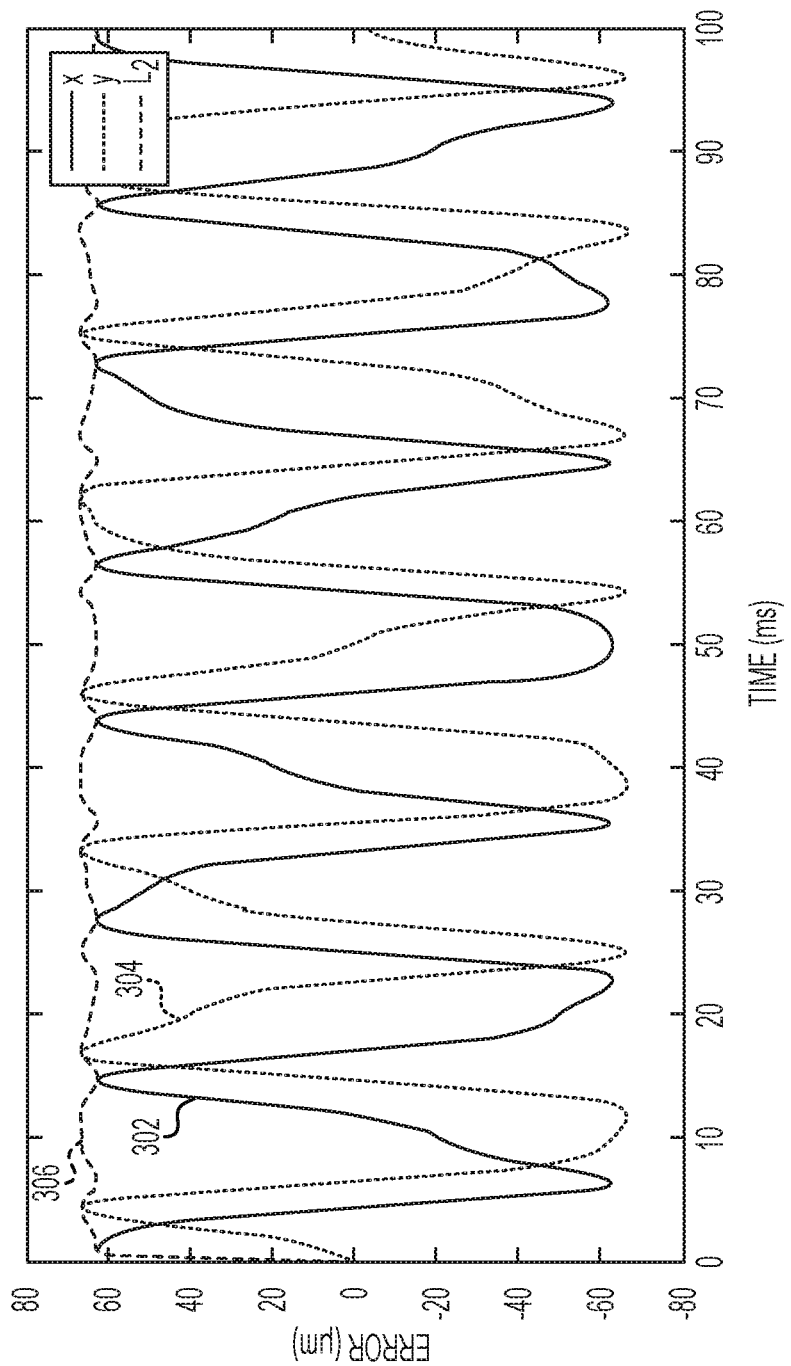
FIG. 3B is a diagram showing example error values for a galvanometer associated having the transfer function shown in FIG. 3A, without the use of a system inverting controller (SIC).

FIG. 3B is a diagram showing example error values for a scanning pattern run on a galvanometer having the transfer function shown in FIG. 3A, without the use of a system inverting controller (SIC). In the example shown, the error values for the x-direction are shown by 302, the error values for the y-direction are shown by 304, and the $L_2$ norm error values represented by the following equation:

$$L_2(x_1, x_2, \ldots, x_n) = \sqrt{x_1^2 + x_2^2 + \ldots x_n^2} \quad \text{Eq. (2.3)}$$

are shown by 306. The example error values shown in FIG. 3B range between +/−80 µm.

Figure 3C:
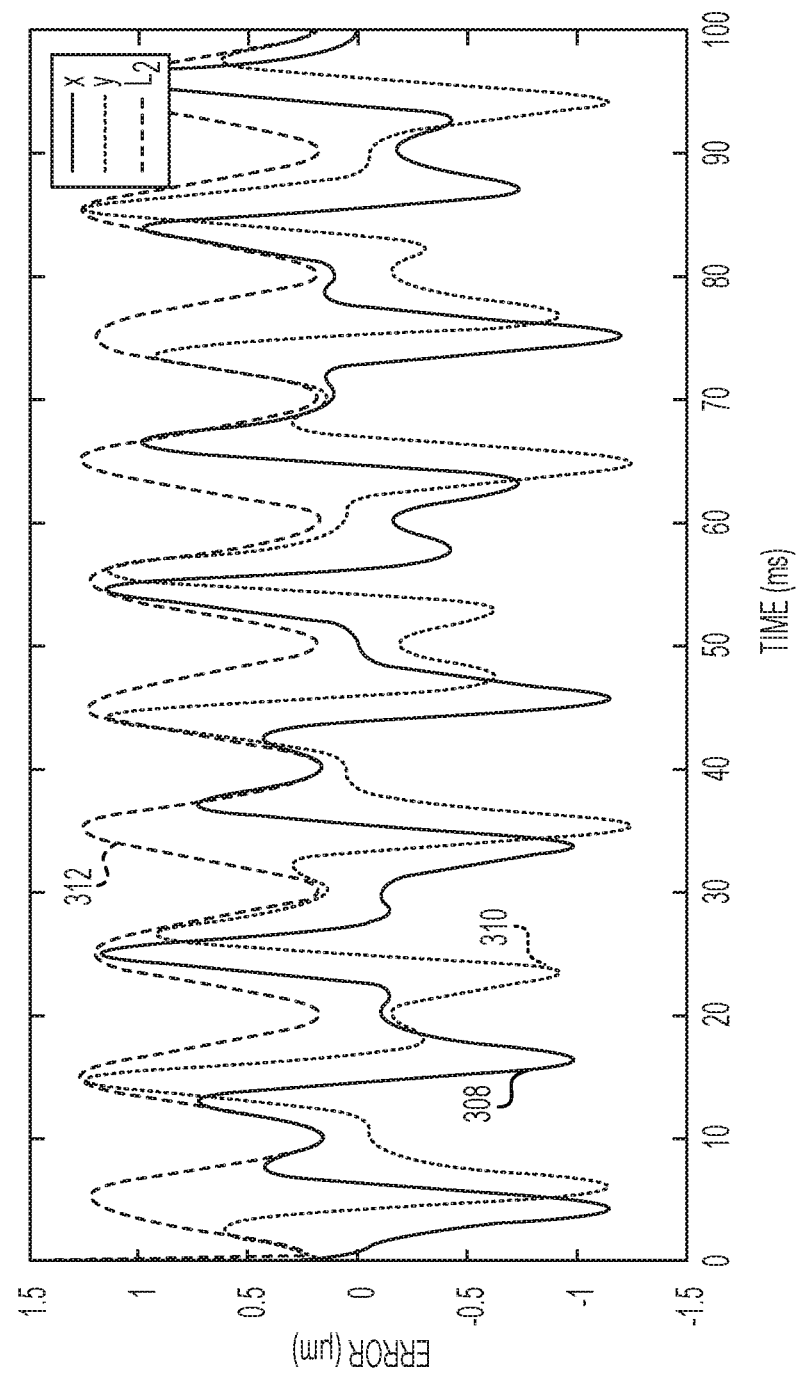
FIG. 3C is a diagram showing example error values for a galvanometer associated having the transfer function shown in FIG. 3A, with the use of a system inverting controller (SIC).

FIG. 3C is a diagram showing example error values for a scanning pattern run on a galvanometer having the transfer function shown in FIG. 3A, with the use of a system inverting controller (SIC) before the galvanometer (e.g., as shown in FIG. 1). In the example shown, the error values for the x-direction are shown by 308, the error values for the y-direction are shown by 310, and the $L_2$ norm error values are shown by 312. The example error values shown in FIG. 3C range between +/−1.5 µm, which is a substantial improvement over the error values shown in FIG. 3B.

Figure 4:
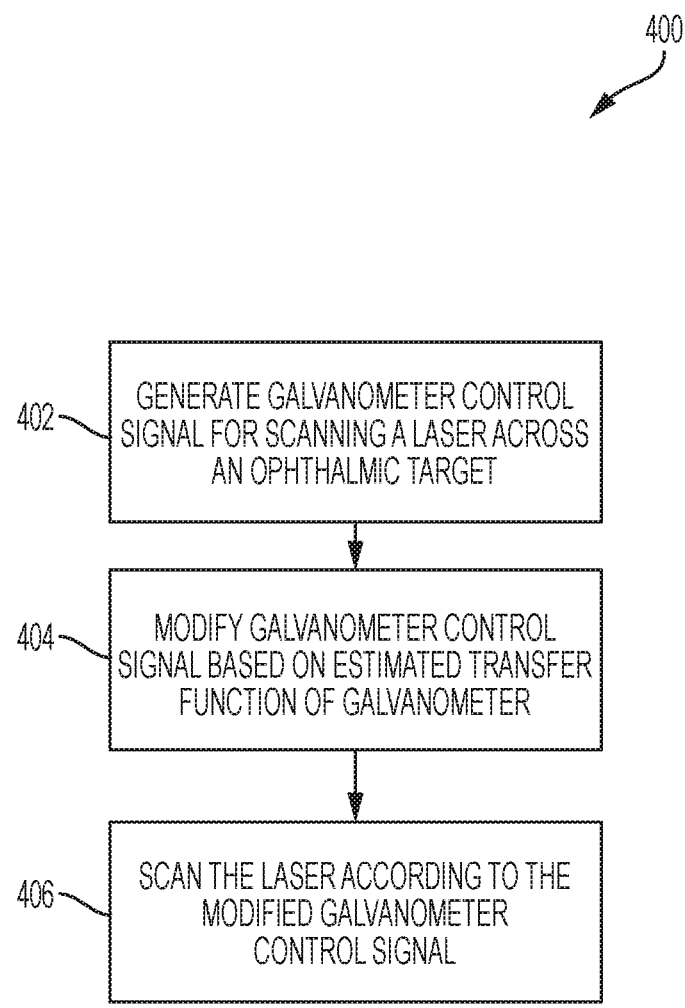
FIG. 4 is a flow diagram of an example process for scanning a laser based on galvanometer control signals modified using a system inverting controller (SIC).

FIG. 4 is a flow diagram of an example process for scanning a laser based on galvanometer control signals modified using a system inverting controller (SIC). Operations in the example process 400 may be performed by components of an ophthalmic diagnostic system (e.g., the control system 110, SIC 120, or galvanometer 130 of the ophthalmic diagnostic system 100 of FIG. 1). The example process 400 may include additional or different operations, and the operations may be performed in the order shown or in another order. In some cases, one or more of the operations shown in FIG. 4 are implemented as processes that include multiple operations, sub-processes, or other types of routines. In some cases, operations can be combined, performed in another order, performed in parallel, iterated, or otherwise repeated or performed another manner.

At 402, galvanometer control signals for scanning a laser across an ophthalmic target are generated. The galvanometer control signals may be received from a control system and may be formatted in any suitable manner. In some cases, the galvanometer control signals may be an input voltage signal that controls a galvanometer and indicates a relative location of one or more optical elements that are used to scan the laser. For instance, referring to the example shown in FIG. 1, the control system 110 may provide a voltage signal that controls an orientation of the mirrors 134, 136, the lenses 139 of the Z-scanner 138, or both to scan a laser from the laser source 140 across the ophthalmic target 150.

At 404, the galvanometer control signals are modified based on an estimated transfer function of a galvanometer. The galvanometer control signals may be modified by a system inverting controller (SIC) before the galvanometer in a signal chain. For instance, referring to the example shown in FIG. 1, the SIC 120 is between the control system 110 and the galvanometer 130 in the signal chain, and modifies galvanometer control signals generated by the control system 110. In some embodiments, the estimated transfer function is a first order transfer function, and may be equivalent to $y_{i+i} = a\Delta t(kx_i - y_i) + y_i$, where a and k are parameters of the first order transfer function, $x_i$ is the input signal of the galvanometer at time t=i, $y_i$ is the output of the galvanometer at time t=i, and $\Delta t$ is the elapsed time between t=(i−1) and t=i. In some embodiments, the SIC may be configured to modify the galvanometer control signals based on a gradient of decent for parameters of the estimated transfer function, such as, for example, in the manner described below with respect to FIG. 5.

At 406, a laser is scanned according to the modified galvanometer control signal. The laser may be scanned by one or more optical elements of the galvanometer. For instance, referring to the example shown in FIG. 1, an orientation of the mirrors 134, 136, the lenses 139 of the Z-scanner 138, or a combination thereof may be controlled by the modified galvanometer control signals form the SIC 120 to scan a laser from the laser source 140 across the ophthalmic target 150. In some embodiments, the scanning pattern may resemble the ideal scanning pattern 202 of FIG. 2A, with reduced error.

Figure 5:
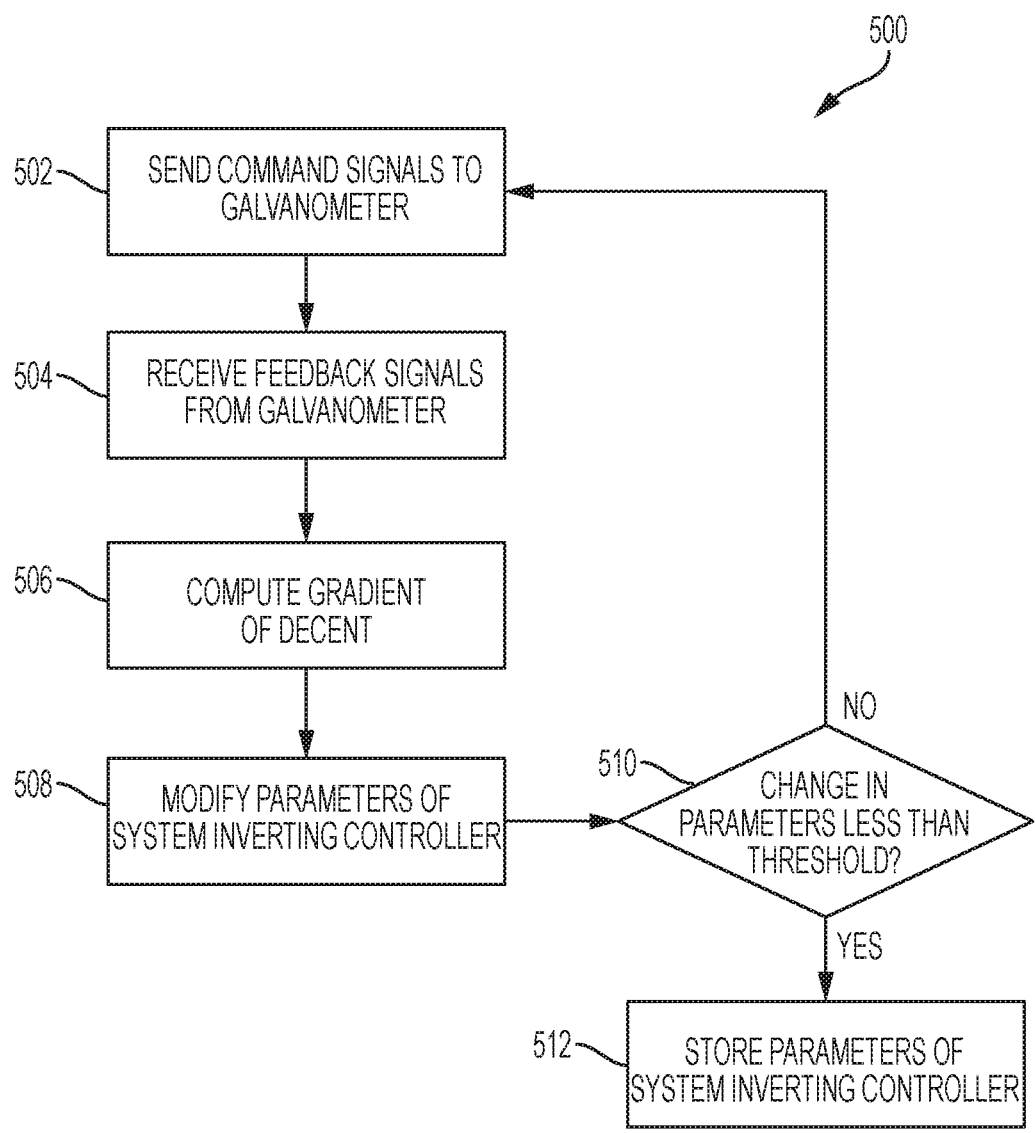
FIG. 5 is a flow diagram of an example process for configuring a system inverting controller (SIC) for use in a laser scanning system.

FIG. 5 is a flow diagram of an example process for configuring a system inverting controller (SIC) for use in a laser scanning system. Operations in the example process 500 may be performed by components of an ophthalmic diagnostic system (e.g., the control system 110, SIC 120, or galvanometer 130 of the ophthalmic diagnostic system 100 of FIG. 1). The example process 500 may include additional or different operations, and the operations may be performed in the order shown or in another order. In some cases, one or more of the operations shown in FIG. 5 are implemented as processes that include multiple operations, sub-processes, or other types of routines. In some cases, operations can be combined, performed in another order, performed in parallel, iterated, or otherwise repeated or performed another manner.

At 502, command signals are sent to a galvanometer. The command signals may be formatted similar to the galvanometer control signals described above. For example, the command signals may include an input voltage signal that controls a galvanometer and indicates a relative location of one or more optical elements that are used to scan a laser.

At 504, feedback signals are received from the galvanometer. The feedback signals may be formatted in any suitable manner. In some cases, the feedback signals are formatted in the same manner as the command signals sent at 502. For example, the feedback signals may include the output signals from the galvanometer that are based on the command signals sent at 502.

At 506, a gradient of decent is computed. This may be done by first computing a baseline error value:

$$E_j^0 = \sum_{i=1}^{N} (\vec{x}_{i,cmd} - \vec{x}_{i,fb})^2 \quad \text{Eq. (3.1a)}$$

which, because the terms are vectors, is equivalent to $$E_j^0 = \sum_{i=1}^{N} (x_{i,cmd} - x_{i,fb})^2 + (y_{i,cmd} - y_{i,fb})^2. \quad \text{Eq. (3.1b)}$$

Each of the parameters of the estimated transfer function implemented by an SIC varied, one by one, and associated error terms $E_j^n$ may be determined from each $n^{th}$ parameter. In some embodiments, the parameters of the estimated transfer function include the values a, k described above. In some embodiments, the parameters of the estimated transfer function include a bias value b that is additive to the transfer function described above. For each $n^{th}$ parameter, a gradient value may be determined by the equation:

$$G^n = \frac{E_j^n - E_j^0}{\Delta p} \quad \text{Eq. (3.2)}$$

where Δp represents the variation in the $n^{th}$ parameter. The process may be repeated for each of the n parameters, with the parameters being reset each time (i.e., only one parameter is varied for each round relative to the initial set of parameters).

At 508, parameters of a system inverting controller are modified. The parameters may be modified based on the gradient values determined at 506. For example, where the parameters are represented by the array $\vec{p} = [k_x, a_x, k_y, a_y]$ (k and a described above have x- and y-components; k and a may also have a z-component, in some cases), the parameter may be modified in the direction opposite the gradient values, such as:

$$\overrightarrow{p_{t+1}} = \vec{p_t} + \alpha \vec{G} \qquad \text{Eq. (3.3)}$$

where $\alpha$ represents a constant value and $\vec{G}$ represents an array that includes the values, for each parameter, of the gradients determined according to Equation 3.2 above.

At 510, it is determined whether the change in the parameters is less than a threshold. For instance, the value $|\overrightarrow{p_{t+1}} - \vec{p_t}|$ may be compared with a threshold error value $\varepsilon$. If the value $|\overrightarrow{p_{t+1}} - \vec{p_t}|$ is greater than the threshold error value $\varepsilon$, then the process may proceed to 502, and the process may be repeated. This process may be repeated iteratively until the value $|\overrightarrow{p_{t+1}} - \vec{p_t}|$ is less than the threshold error value $\varepsilon$ If the value $|\overrightarrow{p_{t+1}} - \vec{p_t}|$ is less than the threshold error value $\varepsilon$, then the new values of the parameters ($\overrightarrow{p_{t+1}}$) is stored at 512. Storing the parameters may include storing the parameters at a SIC such that the new set of parameters are used in a next iteration of a laser scanning process, such as the process 400 of FIG. 4.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer-readable storage medium for execution by, or to control the operation of, data-processing apparatus. A computer-readable storage medium can be, or can be included in, a computer-readable storage device, a computer-readable storage substrate, a random or serial access memory array or device, or a combination of one or more of them. Moreover, while a computer-readable storage medium is not a propagated signal, a computer-readable storage medium can be a source or destination of computer program instructions encoded in an artificially generated propagated signal. The computer-readable storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The computer system may include one or more data processing apparatuses coupled to computer-readable media storing one or more computer programs that may be executed by the one or more data processing apparatuses, and one or more interfaces for communicating with other computer systems.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Embodiments of the present disclosure provide systems and methods for obtaining diagnostic information about an ophthalmic target that may overcome limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations, or improvements therein may be subsequently made by those skilled in the art which alternatives, variations and improvements are also intended to be encompassed by the following claims.

What is claimed is:

1. An ophthalmic diagnostic system, comprising:
   a laser source;
   a galvanometer comprising:
      one or more optical elements; and
      one or more galvanometer controllers configured to manipulate an orientation of the one or more optical elements to scan the output of the laser source across an ophthalmic target based on galvanometer control signals; and
   a system inverting controller (SIC) coupled to the galvanometer, the SIC configured to modify input galvanometer control signals based on an estimated transfer function of the galvanometer and provide the modified galvanometer control signals to the galvanometer;
   wherein the SIC is further configured to receive feedback signals from the galvanometer and modify the input galvanometer control signals based on the feedback signals; wherein the SIC is configured to modify the galvanometer control signals based on a gradient of decent for parameters of the estimated transfer function; wherein the estimated transfer function is a first order transfer function; and wherein the estimated transfer function is equivalent to $y_{i+1}=a\Delta t(kx_i-y_i)+y_i$, where a and k are parameters of the first order transfer function, $x_i$ is the input signal of the galvanometer at time t=i, $y_i$ is the output of the galvanometer at time t=i, and $\Delta t$ is the elapsed time between t=(i−1) and t=i.

2. The system of claim 1, wherein the one or more optical elements comprise a set of mirrors configured to scan the output of the laser source in a first and second direction.

3. The system of claim 2, wherein the one or more optical elements comprise a set of lenses configured to scan the output of the laser source in a third direction orthogonal to the first and second directions.

4. The system of claim 1, wherein the laser source comprises an optical coherence tomography (OCT) engine.

5. The system of claim 1, wherein the laser source comprises a femtosecond laser.

6. A method of scanning a laser of an ophthalmic diagnostic system, comprising:
receiving galvanometer control signals at a system inverting controller (SIC);
modifying, by the SIC, the galvanometer control signals based on an estimated transfer function of a galvanometer controller;
providing the modified galvanometer control signals to a galvanometer; and
manipulating, by the galvanometer, one or more optical elements to scan a laser based on the modified galvanometer control signals;
receiving, at the SIC, feedback signals from the galvanometer, wherein modifying the galvanometer control signals is based on the feedback signals;
wherein modifying the galvanometer control signals is based on a gradient of decent for parameters of the estimated transfer function; wherein the estimated transfer function is a first order transfer function; and wherein the estimated transfer function is equivalent to $y_{i+1}=a\Delta t(kx_i-y_i)+y_i$, where a and k are parameters of the first order transfer function, $x_i$ is the input signal of the galvanometer at time t=i, $y_i$ is the output of the galvanometer at time t=i, and $\Delta t$ is the elapsed time between t=(i−1) and t=i.

7. The method of claim 6, wherein manipulating the one or more optical elements to scan the laser comprises manipulating an orientation of a set of mirrors in the galvanometer to scan the laser in a first and second direction.

8. The method of claim 7, wherein manipulating the one or more optical elements to scan the laser comprises manipulating a position of one or more lenses to scan the laser in a third direction orthogonal to the first and second directions.

* * * * *